(12) United States Patent
McKinney et al.

(10) Patent No.: US 6,733,761 B2
(45) Date of Patent: May 11, 2004

(54) MYCOBACTERIAL ISOCITRATE LYASE GENE AND USES THEREOF

(75) Inventors: John D. McKinney, Bronx, NY (US); William R. Jacobs, Jr., City Island, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 10/029,715

(22) Filed: Dec. 20, 2001

(65) Prior Publication Data

US 2002/0151031 A1 Oct. 17, 2002

Related U.S. Application Data

(63) Continuation of application No. 09/054,680, filed on Apr. 3, 1998, now Pat. No. 6,387,694.
(51) Int. Cl.[7] .................. A61K 39/04; A61K 48/00; A61K 39/02; C07H 21/02; C07H 21/04
(52) U.S. Cl. .................. 424/248.1; 424/93.2; 424/93.4; 424/234.1; 435/440; 435/441; 435/446; 435/449; 435/450; 435/454; 435/471; 435/320.1; 536/23.1; 536/23.2; 536/23.7
(58) Field of Search .................. 424/234.1, 248.1, 424/93.2, 93.4; 435/440, 441, 446, 449, 450, 454, 471, 320.1; 536/23.1, 23.2, 23.7

(56) References Cited

U.S. PATENT DOCUMENTS

| | | |
|---|---|---|
| 5,504,005 A | 4/1996 | Bloom et al. |
| 5,686,590 A | 11/1997 | Jacobs et al. |
| 5,773,267 A | 6/1998 | Jacobs et al. |
| 5,783,386 A | 7/1998 | Jacobs et al. |
| 5,854,055 A | 12/1998 | Bloom et al. |
| 5,976,844 A | 11/1999 | Kasler et al. |
| 6,387,694 B1 | 5/2002 | McKinney et al. |

FOREIGN PATENT DOCUMENTS

| | | |
|---|---|---|
| WO | WO 92/22326 | 12/1992 |
| WO | WO 98/41533 | 9/1998 |

OTHER PUBLICATIONS

Kalpana et al., Insertional mutagenesis and illegitimate recombination in mycobacteria PNAS, 88: 5433–5437, Jun. 1991.

Seshadri et al., Isociatrate lyase in mycobacteria. Indian J. Biochemistry & Biophysics 13/1: 95–96, 1976.

Graham et al., Identification of Mycobacterium tuberculosis RNAs synthesized in response to phagocytosis by human macrophages by selective capture of transcribed sequences (SCOTS). PNAS, 96/20: 11554–11559, 1999.

Fsihi et al., The *Mycobacterium leprae* genome: systematic sequence analysis identifies key catabolic enzymes, ATP–dependent transport systems and a novel polA locus associated with genomic variability. Molecular Microbiol, 16/5: 909–919, 1995.

Wayne et al., Glyoxylate metabolism and adaptation of Mycobacterium tuberculosis to survival under anaerobic conditions. Infection & Immunity, 37/3: 1042–1049, 1982.

Cole et al., Deciphering the biology of Mycobacterium tuberculosis from the complete genome sequence. Nature, 393 (6685): 537–544, 1998.

Bharadwaj et al., Metabolic studies on mycobacteria. IV. Assay of isocitrate lyase and malate synthase activity in *M. leprae*. Indian J. Leprosy, 59/2:158–162, 1987.

Kannan et al., Metabolic studies on mycobacteria—II. Glyoxylate by–pass (TCA cycle) enzymes of slow and fast growing mycobacteria. Indian J. Leprosy, 57/3; 542–548, 1985.

Vereecke et al., Cloning and sequence analysis of the gene encoding isocitrate lyase from *Rhodococcus fascians*. Gene, 145: 109–114, 1994.

*Primary Examiner*—Rodney P Swartz
(74) *Attorney, Agent, or Firm*—Amster, Rothstein & Ebenstein LLP

(57) ABSTRACT

The present invention provides a purified and isolated nucleic acid encoding mycobacterial isocitrate lyase, as well as mutated forms of the nucleic acid. Further provided are purified and isolated isocitrate lyase proteins and mutated isocitrate lyase proteins. Additionally, the present invention provides vectors which comprises nucleic acid sequences encoding mycobacterial isocitrate lyase and mutated forms of this nucleic acid, as well as host cells containing these vectors. Also provided is a mycobacterium containing one or more mutations in its isocitrate lyase gene. Further provided by the present invention are agents that inhibit the activity or expression of a mycobacterial lyase protein, a method of identifying these, and a method of producing them. Finally, the present invention also provides a method of identifying genes required for persistence of mycobacteria.

13 Claims, 8 Drawing Sheets

FIGURE 1A

*Mycobacterium tuberculosis icl* gene nucleotide sequence:

ATGTcTGTcGTCGGCACCCCGAAGAGCGCGGAGCAGATCCAGCAGGAATGGGACACGAACCCGCGC
TGGAAGGACGTCACCCGCACCTACTCCGCCGAGGAcGTcGTCGCCCTCCAGGGCAGCGTGGTCGAG
GAGCACACGCTGGCCCGCCGCGGTGCGGAGGTGCTGTGGGAGCAGCTGCACGACCTCGAGTGGG
TCAACGCGCTGGGCGCGCTGACCGGCAACATGGCCGTCCAGCAGGTGCGCGCCGGCCTGAAGGC
CATCTACCTGTCGGGCTGGCAGGTCgCCGGCgATgCCAACCTGTCCGGGCACACCTACCCCGACCAg
AGCCTGTATCCCGCCAACTCGGTGCCGCAGGTGGTCCGCCGGATCAACAACGCACTGCAGCGCgCC
GACCAgATCgCCAAGATCGAGGGCGATACTTCGGTGGAgAACTGGCTGGCGCCGATTGTCgCCgACg
GCGAgGCCGGCTTTGGCGGCGCgCTCAACgTCTACgAgCTGCAgAAAGCCCTGATCgCCGCGGGCGT
TGCGGGTTCgCACTGGGAGGACCAgTTGGCCTCTGAgAAgAAgTGCGGCCACCTGGGCGGCAAGGT
GTTGATCCCGACCCAgCAgCACATCCGCACTTTGACgTCTGCTCgGCTCgCGGCCGATGTGGCTGATg
TTCCCaCGGTGGTgATcGCCCgTACCGACgCCGAgGCGGcCaCgCTGATcACCTCCgACGTCgAcGAGC
GCGACCAGCCGTTcATCACCGGCGAGCGCACCCGGGAAGGcTTcTACCGCACCAAGAACGGCATCG
AGCCTTGCATCGCTCGGGCGAAGGCCTACGCCCCGTTCGCCGACTTGATcTGGATGGAgACCGGTA
CCCCGGACCTCgAgGCCGCCCGGCagTTCTCCgAgGCGGTCAAGGcGGAgTaCCCGGAcCAgATGCTG
GCCTACAACTGCTCGCCATCGTTCAACTGGAAAAAgCACCTCgACgAcGCCaCCaTCgCCAAgTTCCAg
AAGGAgCTGGCAGCCATGGGCTTCAAgTTCCAgTTCATCACGCTGGCCGGcTTCCATGCGCTGAACTA
CTCgATGttcgaTCTGGccTACGGcTACGCCCAGAACCAGATGAGCGCGTATGTCGAACTGCAGGAACG
CGAGTTCGCCGCCGAAGAACGGGGcTACACCGCGACCAAGCACCAGCGCGAGGTCGGCGCCGGCT
ACTTCGACCGGATTGCCACCACCGTGGACCCGAATTCGTCGACCACCGCGTTGACCGGTTCCACCG
AAgAgGGCCAGTTCCACTAg

FIGURE 1B

*Mycobacterium tuberculosis* ICL protein sequence (428 amino acids):

MSVVGTPKSAEQIQQEWDTNPRWKDVTRTYSAEDVVALQGSVVEEHTLARRGAEVLWEQLHDLEWVNA
LGALTGNMAVQQVRAGLKAIYLSGWQVAGDANLSGHTYPDQSLYPANSVPQVVRRINNALQRADQIAKIE
GDTSVENWLAPIVADGEAGFGGALNVYELQKALIAAGVAGSHWEDQLASEKKCGHLGGKVLIPTQQHIRT
LTSARLAADVADVPTVVIARTDAEAATLITSDVDERDQPFITGERTREGFYRTKNGIEPCIARAKAYAPFADL
IWMETGTPDLEAARQFSEAVKAEYPDQMLAYNCSPSFNWKKHLDDATIAKFQKELAAMGFKFQFITLAGF
HALNYSMFDLAYGYAQNQMSAYVELQEREFAAEERGYTATKHQREVGAGYFDRIATTVDPNSSTTALTG
STEEGQFH

FIGURE 2A

Mycobacterium smegmatis icl gene nucleotide sequence:

ATGTcGACCGTTGGCACCCCGAAGTCCCCCGAGCAGATCCAGCACGACTGGGATCACAACCCCCGC
TGGAAGGGCATCAAGCGCGACTACACCCCCGAGGACGTcGTGGCCCTGCAGGGCAcCGTCGTCGAg
gAGCACACCCTGGCCCGCCGCGGCGCCGAgGTGCTGTGGGAGCAgCTGCACGACATGGACTTCGTC
AACGCGCTCGGCGCGCTGACCGGCAACATGGCCGTCCAgCAgGTTCGCGCGGGCCTCAAGGCCAT
CTACCTGTCCGGCTGGCAGGTCgCCGGTGACgCCAACCTGTCCGGTCACACCTACCCCGACCAGAg
CCTGTACCCGGCCAACTCGGTGCCGCAGGTGGTCCGCCGCATCAACAACGCGCTGCTGCGCGCCG
ACgAgATCgCCAAGGTCGAgGGCGACACCTCgGTGGAgAACTGGCTGGCTCCgATCgTCgCCgAcgGcG
AgGCCGGCTTCgGTGGTGCCCTCAACGTCTACgAgCTGCAGAaGGCGATGATCGCCGCGGGTGTCG
CGGGCTCGCACTGGGAAGATCAGcTGGCCTCGGAGAAGAAGTGCGGCCACCTCGGTGGCAAGGTG
CTGATCCCGACCCAGCAGCACATCCGCACCCTGACCTcGGCGCGCCTGGCGGCCGAcGTGGCCGAc
GTGCCCACCGTcGTCATcGCCCGCACCGACGCCGAGGCCGCCACGCTGATCACGTCCGACGTCGAC
GAgCGCGACCAGCCGTTCaTCACCGGTGAGCGCACCAAGGAAgGCTTCTTCCGCGTGAAgAACGGC
CTGGAgcCCTGCATCgCGCGCGCCAAGGCCTACgCGCCGTACTCCGACCTGATCTGGATGGAGACC
GGCACgCCGGATcTCGAGCTCGCCAAGAAGTTCGCCGAGGGCGTCAAGGCGGAGTTCCCCGACCA
GATGcTGGCCTACAACTGCTCGCCGTCGTTCAACTGGAAGAAGCACCTcGACGACGCCACCATCGCG
AAGTTCCAGAAGGAACTGGGCGCCATGGGCTTCAAGTTCCAGTTCATCACGCTGGCCGGCTTCCAC
GCGCTCAACTACTCGATGTTCGATcTGGCCTACGGcTACGCCCGCAACCAGATGAGCGCGTACGTCG
AACTGCAGGAGCGCGAGTTCGCTGCCGAGGaGCGCGGCTACACCGCCACCAAGCACCAGCGCGAG
GTGGGTGCCGGCTACTTCGACCGCATCGCCACCACGGTCGAcCCCAACAGCTCGACCACCGCGCTC
GCGGGCTCGACCGAAgAgGGTCAGTTCCACTGA

FIGURE 2B

Mycobacterium smegmatis ICL protein sequence (428 amino acids):

MSTVGTPKSPEQIQHDWDHNPRWKGIKRDYTPEDVVALQGTVVEEHTLARRGAEVLWEQLHDMDFVNA
LGALTGNMAVQQVRAGLKAIYLSGWQVAGDANLSGHTYPDQSLYPANSVPQVVRRINNALLRADEIAKVE
GDTSVENWLAPIVADGEAGFGGALNVYELQKAMIAAGVAGSHWEDQLASEKKCGHLGGKVLIPTQQHIR
TLTSARLAADVADVPTVVIARTDAEAATLITSDVDERDQPFITGERTKEGFFRVKNGLEPCIARAKAYAPYS
DLIWMETGTPDLELAKKFAEGVKAEFPDQMLAYNCSPSFNWKKHLDDATIAKFQKELGAMGFKFQFITLA
GFHALNYSMFDLAYGYARNQMSAYVELQEREFAAEERGYTATKHQREVGAGYFDRIATTVDPNSSTTAL
AGSTEEGQFH

*M. tuberculosis*

*M. smegmatis*

FIGURE 5

```
Mtb    1  MSVVGTPKSAEQIQQEWDTNPRWKDVTRTYGAEDVVALQGEVVEEHTLARRGAEV
Msm    1  MSTVGTPKSPEQIQHDWDHNPRWKGIKRDYTPEDVVALQGTVVEEHTLARRGAEV
Rfa    1  MSTTGTPKTTAEIQQDWDTNPRWKGVTRNFTAQQVSDLQGTVVEEATLARRGSE

Mtb   56  LWEQLHDLEWVNALGALTGNMAVQQVRAGLKAIYLSGWQVAGDANLSGHTYPDQS
Msm   56  LWEQLHDMDFVNALGALTGNMAVQQVRAGLKAIYLSGWQVAGDANLSGHTYPDQS
Rfa   56  LWDLVNNEDYINSLGALTGNQAVQQIRAGLQAIYLSGWQVAGDANLSGHTYPDQS

Mtb  111  LYPANSVPQVVRRINNALQRADQIAKIEGDTSVENWLAPIVADGEAGFGGALNVY
Msm  111  LYPANSVPQVVRRINNALLRADEIAKVEGDTSVENWLAPIVADGEAGFGGALNVY
Rfa  111  LYPANSVPSVVRRINNALLRADEIAKIEGDTSVKNWVAPIVADNEAGFGGALNAY

Mtb  166  ELQKALIAAGVAGSHWEDQLASEKKCGHLGGKVLIPTQQHIRTLTSARLAADVAD
Msm  166  ELQKAMIAAGVAGSHWEDQLASEKKCGHLGGKVLIPTQQHIRTLTSARLAADVAD
Rfa  166  ELQKAMIVAGAAGVHWEDQLASEKKCGHLGGKVLIRTQQHIRTLTSARLADVAD

Mtb  221  VPTVVIARTDAEAATLITSDVDERDQPFITGERTREGFYRTKNGIEPCIARAKAY
Msm  221  VPTVVIARTDAEAATLITSDVDERDQPFITGERTKEGFFRVKNGEEPCIARAKAY
Rfa  221  VPBVHLARTDAEAATLITSDVDERDREFIDGTRTAEGFFCVKNGIEPCIARAKAY

Mtb  276  APFADLIWMETGTPDLEAAROFSEAVKAEIPDQMLAYNCSPSFNWKKHLDDATIA
Msm  276  APYSDLIWMETGTPDLELAKKFAEGVKAEFPDQMLAYNCSPSFNWKKHLDDATIA
Rfa  276  APYADLIWMETGVPDLEVAKKFSEBVRSEFPDQFLAYNWSPSFNWKAHLDDATIA

Mtb  331  KFQKELAAMGFKFQFITLAGFHALNYSMFDLAYGYAQNQMSAYVELQEREFAAEE
Msm  331  KFQKELGAMGFKFQFITLAGFHALNYSMFDLAYGYARNQMSAYVELQEREFAAEE
Rfa  331  KFQKELGAMGFKFQFITLAGFHJLNYGMFDLAYGYAQNQMSAYVELQEREFAAEE

Mtb  386  RGYTATKHQREVGAGYFDRIATTVDPNSSTTALTGSTEEGQFH
Msm  386  RGYTATKHQREVGAGYFDRIATTVDPNSSTTALTGSTEEGQFH
Rfa  386  RGYTATKHQREVGAGYFDRIATTVDPNSSTTALAGSTEEGQFH
```

MYCOBACTERIAL ISOCITRATE LYASE GENE AND USES THEREOF

This patent application is a continuation of U.S. application Ser. No. 09/054,680, filed Apr. 3, 1998, and entitled "MYCOBACTERIAL ISOCITRATE LYASE GENE AND USES THEREOF", now U.S. Patent No. U.S. Pat. No. 6,387,694 B1, issued May 14, 2002, the contents of which are incorporated herein by reference in their entirety.

STATEMENT OF GOVERNMENT INTEREST

This invention was made with government support under NIH Grant No. AI26170. As such, the government has certain rights in this invention.

BACKGROUND OF THE INVENTION

Pulmonary tuberculosis initiates with the inhalation and retention in the lung alveoli of a "droplet nucleus" containing from 1–10 tubercle bacilli. Most cases of human tuberculosis originate from a single primary lesion in the lung parenchyma; the number of bacilli initiating an infection is therefore extremely small (Medlar). Patent tuberculous disease develops only after expansion of this initially small bacillary population by replication within host macrophages. In order to grow, persist, and cause disease, tubercle bacilli must obtain nutrients from the parasitized host. Little is known, however, of the mechanisms involved in nutrient acquisition by tubercle bacilli in vivo. Writing in 1976, Ratledge opined that "[T]he entire subject of in vivo nutrition of bacteria when within the phagocytic cells of the host is probably the largest single area of ignorance in the whole of our knowledge concerning the physiology of the mycobacteria. Clearly this is a crucial area where knowledge should be sought as it is only by understanding the true behavior and requirements of the bacteria when growing in vivo that we shall learn how to prevent their multiplication and, hopefully, how to cause their death" (Ratledge, 1976) Unfortunately, the intervening decades have marked little progress in this area. With the advent of molecular genetic tools for the manipulation of the pathogenic mycobacteria, a genetic approach to this problem is now feasible.

In the infected host, *M. tuberculosis* bacilli replicate within host macrophages. Following phagocytosis, tubercle bacilli reside within modified phagosomes that apparently fuse with vacuoles derived from the endosomal compartment (Sturgill-Koszycki et al., 1996) but that fail to acidify fully or to fuse with lysosomes (reviewed in Clemens, 1996). As an intracellular parasite, *M. tuberculosis* would potentially have access to a variety of nutrients that are abundant within the host cell cytoplasm (Wheeler and Ratledge, 1994). The enclosure of tubercle bacilli within tightly apposed membranous vacuoles (Moreira et al., 1997) might, however, limit access to cytoplasmic constituents. This idea was supported by the recent demonstration that a leuD auxotroph of the attenuated bacille Calmette-Guerin (BCG) strain of tubercle bacillus was incapable of replicating in mice (McAdam et al., 1995) or in cultured macrophages (Bange et al., 1996). Although *M. tuberculosis* is not a nutritionally fastidious organism, bacillary growth does require a carbon substrate(s) to provide building blocks for biosynthetic reactions and energy for metabolism. In vitro, *M. tuberculosis* is capable of utilizing a wide range of carbon substrates, including carbohydrates, amino acids, and C2 carbon sources such as acetate and fatty acids (Wayne, 1994). It is not known which of these substrates are available to *M. tuberculosis* replicating within the confines of the phagosomal compartment.

Extensive biochemical studies have been made of tubercle bacilli isolated directly from the lungs of chronically infected mice (reviewed in Segal 1984). Using manometry, Segal and Bloch (1956) showed that these "in vivo grown" bacilli displayed a vigorous respiratory response to fatty acids but failed to respond to a variety of other substrates. In contrast, respiration of tubercle bacilli grown in vitro was readily stimulated by both glucose and glycerol, which are the preferred substrates for in vitro cultivation of tubercle bacilli. These observations suggested that tubercle bacilli in vivo may be adapted to utilization of fatty acids and may repress pathways for utilization of other carbon sources. Later studies revealed that in vivo grown bacilli retained the ability to oxidize $^{14}C$-glucose to $^{14}C$—$CO_2$, but that addition of exogenous glucose suppressed the respiration of endogenous substrates presumably including fatty acids (Artman and Bekierkunst, 1960).

Two specialized pathways are required for utilization of fatty acids as sole carbon source. The b-oxidation pathway catalyzes the breakdown of fatty acids to assimilable acetyl CoA units, which are further oxidized via the Krebs cycle (Clark and Cronan, 1996). The glyoxylate shunt is an anaplerotic pathway for replenishment of essential Krebs cycle intermediates consumed by biosynthetic pathways during growth on $C_2$ carbon sources such as fatty acids and acetate (Cronan and LaPorte, 1996). This anaplerotic function is subsumed by pyruvate carboxylase when cells are grown on carbohydrates. Wheeler and Ratledge (1988) found that in vivo grown mycobacteria readily oxidized $[^{14}C]$-palmitate to $[^{14}C]$—$CO2$, implying that the enzymes required for b-oxidation of fatty acids were expressed in vivo. (In fact, evolution of $[^{14}C]$—$CO2$ from $[^{14}C]$-palmitate is the basis of the widely used "BACTEC" system for detection of *M. tuberculosis* in clinical specimens [Heifets and Good, 1994].) In addition, these authors demonstrated expression of both enzymes of the glyoxylate shunt (malate synthase and isocitrate lyase) by in vivo grown mycobacteria. In *Escherichia coli*, expression of the enzymes of the b-oxidation pathway and of the glyoxylate shunt is under transcriptional control: transcription is repressed during growth on carbohydrates and is induced during growth on fatty acids. Although these enzymes and their regulation have been characterized only partially in mycobacteria, their expression by in vivo grown bacilli suggests that fatty acids may be utilized in vivo. If so, then the b-oxidation pathway and the glyoxylate shunt may be essential for in vivo growth or persistence of tubercle bacilli.

SUMMARY OF THE INVENTION

The present invention provides a purified and isolated nucleic acid encoding mycobacterial isocitrate lyase. The present invention specifically provides for nucleic acid sequences encoding mycobacterial isocitrate lyase that are obtained from *M. tuberculosis* and *M. smegmatis*. Also provided by the present invention are mutated nucleic acid sequences encoding mycobacterial isocitrate lyase.

Additionally, the present invention provides vectors which comprises the nucleic acid sequences encoding mycobacterial isocitrate lyase of the present invention, and vectors which comprises the mutated nucleic acid sequences encoding mycobacterial isocitrate lyase of the present invention, as well as host cells containing these vectors.

Further provided by the present invention is an agent that inhibits the activity or expression of a mycobacterial lyase protein, a method of identifying agents that inhibit the activity or expression of a mycobacterial lyase protein, and a method of producing the agents.

Finally, the present invention provides a method of identifying genes required for persistence of mycobacteria.

BRIEF DESCRIPTION OF THE FIGURES

FIG. 1A sets forth the nucleotide sequence (SEQ ID NO:1) of the M. tuberculosis isocitrate lyase gene.

FIG. 1B sets forth the amino acid sequence (SEQ ID NO:2) of the M. tuberculosis isocitrate lyase gene.

FIG. 2A sets forth the nucleotide sequence (SEQ ID NO:3) of the M. smegmatis isocitrate lyase gene.

FIG. 2B sets forth the amino acid sequence (SEQ ID NO:4) of the M. smegmatis isocitrate lyase gene.

FIG. 5 sets forth an amino acid sequence comparison between the M. tuberculosis isocitrate lyase gene (SEQ ID NO:2), the M. smegmatis isocitrate gene (SEQ ID NO:4), and the isocitrate lyase gene from Rhodococcus fasciens (SEQ ID NO:5).

DETAILED DESCRIPTION OF THE INVENTION

Figure 3:
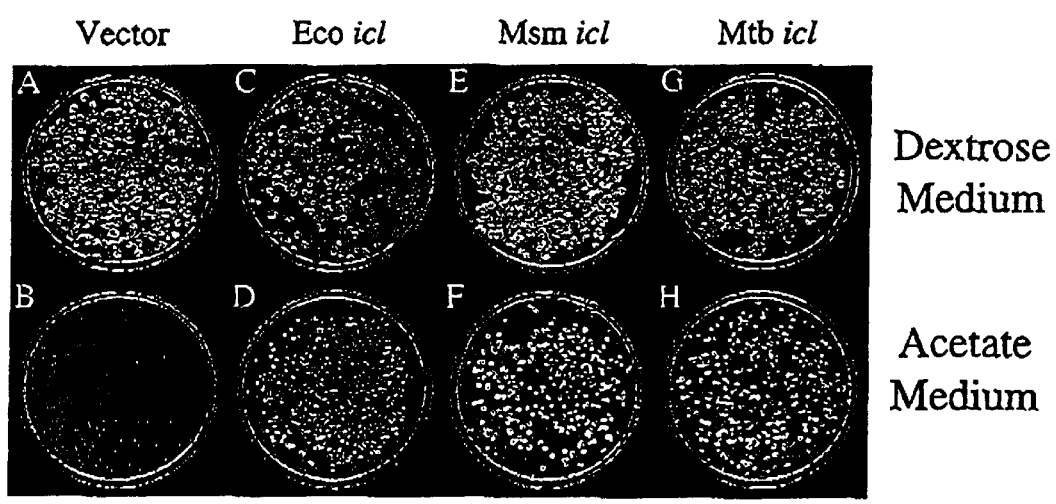
FIGS. 3A–3H set forth the screening results of Ace mutants of M. smegmatis.

The present invention provides a purified and isolated nucleic acid encoding mycobacterial isocitrate lyase. As used herein, the nucleic acid may be genomic DNA, cDNA, or RNA. Due to the degeneracy of the genetic code, the nucleic acid of the present invention also includes a multitude of nucleic acid substitutions which will encode isocitrate lyase.

The present invention specifically provides for a nucleic acid encoding mycobacterial isocitrate lyase that is isolated from Mycobacteria tuberculosis. Preferably, the nucleic acid sequence encoding M. tuberculosis isocitrate lyase encodes the amino acid sequence contained in FIG. 1 (SEQ ID NO:2). More preferably, the M. tuberculosis isocitrate lyase nucleic acid has the nucleotide sequence contained in FIG. 1 (SEQ ID NO:1). The present invention also provides for nucleic acid encoding mycobacterial isocitrate lyase that is isolated from Mycobacteria smegmatis. Preferably, the nucleic acid sequence encoding M. smegmatis isocitrate lyase encodes the amino acid sequence contained in FIG. 2 (SEQ ID NO:4). More preferably, the M. smegmatis isocitrate lyase nucleic acid has the nucleotide sequence contained in FIG. 2 (SEQ ID NO:3).

Further provided by the present invention is a mutated nucleic acid sequence encoding mycobacterial isocitrate lyase. The mutated nucleic acid sequence encoding mycobacterial isocitrate lyase may be isolated from M. tuberculosis, M. smegmatis, M. avium, M. kansasii, M. zenopi, M. simiae, M. gastri, M. szulgai, M. gordonae, M. chelonea, M. leprae, M. bovis-BCG, M. intracellulare, M. habana, M. lufu, M. phlei, M. fortuitum, M. paratuberculosis and M. scrofulaceum. The mutation may be generated in said nucleic acid using methods known to one of skill in the art. Such methods of mutation include, but are not limited to, signature-tagged mutagenesis, transposon mutagenesis, targeted gene disruption, illegitimate recombination and chemical mutagenesis. In a preferred embodiment of the invention, the mutated nucleic acid encoding isocitrate lyase is M. tuberculosis nucleic acid. In a more preferred embodiment on the invention, the mutation in the M. tuberculosis nucleic acid encoding isocitrate lyase is generated by disruption. Disruption of a nucleic acid encoding isocitrate lyase may be performed, for example, by allelic exchange. It is to be understood that the present invention also provides for nucleic acid sequences wherein any or all of the above described mutations coexist in the nucleic acid encoding mycobacterial isocitrate lyase in any combinations thereof.

The mutated nucleic acid sequence encoding mycobacterial isocitrate lyase provided by the present invention may also be obtained from a library of mutants wherein the mutated mycobacteria are generated using methods of mutation which include, but are not limited to, signature-tagged mutagenesis, transposon mutagenesis, targeted gene disruption, illegitimate recombination and chemical mutagenesis. The disruption of a nucleic acid encoding isocitrate lyase may be performed, for example, by allelic exchange.

The mutant nucleic acid sequences encoding mycobacterial isocitrate lyase of the present invention may be prepared in several ways. For example, they can be prepared by isolating the nucleic acid sequences from a natural source, or by synthesis using recombinant DNA techniques. In addition, mutated nucleic acid sequences encoding mycobacterial isocitrate lyase can be prepared using site mutagenesis techniques.

The present invention also provides a vector which comprises the nucleic acid encoding mycobacterial isocitrate lyase of the present invention, and a vector which comprises the mutated nucleic acid encoding mycobacterial isocitrate lyase of the present invention. Such vectors may be constructed by inserting the nucleic acid encoding mycobacterial isocitrate lyase, or the mutated nucleic acid encoding mycobacterial isocitrate lyase into a suitable vector. The term "inserted" as used herein means the ligation of a foreign DNA fragment and vector DNA by techniques such as the annealing of compatible cohesive ends generated by restriction endonuclease digestion or by use of blunt end ligation techniques. Other methods of ligating DNA molecules will be apparent to one skilled in the art.

Vectors may be derived from a number of different sources. They can be plasmids, viral-derived nucleic acids, lytic bacteriophage derived from phage lambda ($\lambda$), cosmids or filamentous single-stranded bacteriophages such as M13. Depending upon the type of host cell into which the vector is introduced, vectors may be bacterial or eukaryotic. Bacterial vectors are derived from many sources including the genomes of plasmids and phage. Eukaryotic vectors are also constructed from a number of different sources, e.g. yeast plasmids and viruses. Some vectors, called shuttle vectors, are capable of replicating in both bacteria and eukaryotes. The nucleic acid from which the vector is derived is usually greatly reduced in size so that only those genes essential for its autonomous replication remain. The reduction in size enables the vectors to accommodate large segments of foreign DNA. Examples of suitable vectors into which the nucleic acid encoding mycobacterial isocitrate lyase or the mutated nucleic acid encoding mycobacterial isocitrate lyase can be inserted include but are not limited to the shuttle vector pYUB412, shuttle vector pMP7, pJM056, pBR322, pUC18, pUC19, pHSV-106, pJS97, pJS98, M13mp18, M13mp19, pSPORT 1, pGem, pSPORT 2, pSV•SPORT 1, pBluescript II, λZapII, λgt10, λgt11, λgt22A, and λZIPLOX. Other suitable vectors are obvious to one skilled in the art.

The vector of the present invention may be introduced into a host cell and may exist in integrated or unintegrated form within the host cell. When in unintegrated form, the vector is capable of autonomous replication. The term "host cell" as used herein means the bacterial or eukaryotic cell into which the vector is introduced. As used herein, "introduced" is a general term indicating that one of a variety of means has been used to allow the vector to enter the intracellular environment of the host cell in such a way that it exists in stable and expressible form therein.

Some bacterial and eukaryotic vectors have been engineered so that they are capable of expressing inserted nucleic acids to high levels within the host cell. Such vectors utilize one of a number of powerful promoters to direct the high level of expression. For example, in vectors for the expression of a gene in a bacterial host cell such as $E.$ $coli$, the lac operator-promoter or the tac promoter are often used. Eukaryotic vectors use promoter-enhancer sequences of viral genes, especially those of tumor viruses. Expression can be controlled in both bacterial and eukaryotic cells using inducible promoters such as the lac operator-promoter in $E.$ $coli$ or metallothionine or mouse mammary tumor virus promoters in eukaryotic cells. As used herein, "expression" refers to the ability of the vector to transcribe the inserted nucleic acid into mRNA so that synthesis of the protein encoded by the inserted nucleic acid can occur.

Vectors may be introduced into host cells by a number of techniques known to those skilled in the art, e.g. electroporation, DEAE dextran, cationic liposome fusion, protoplast fusion, DNA coated-microprojectile bombardment, and infection with recombinant replication-defective retroviruses. The term "transformation" denotes the introduction of a vector into a bacterial or eukaryotic host cell. As such, it encompasses transformation of bacterial cells and transfection, transduction and related methods in eukaryotic cells.

Any one of a number of suitable bacterial or eukaryotic host cells may be transformed with the vector of the present invention. Examples of suitable host cells are known to one skilled in the art and include but are not limited to mycobacterial cells such as *M. tuberculosis, M. smegmatis, M. avium, M. kansasii, M. zenopi, M. simiae, M. gastri, M. szulgai, M. gordonae, M. chelonea, M. leprae, M. bovis-BCG, M. intracellulare, M. habana, M. lufu, M. phlei, M. fortuitum, M. paratuberculosis* and *M. scrofulaceum*, and bacterial cells such as *E.coli* strains c600, c600hfl, HB101, LE392, Y1090, JM103, JM109, dM101, dM107, Y1088, Y1089, Y1090, Y1090(ZZ), DM1, PH10B, DH11S, DH125, RR1, TB1 and SURE, *Bacillus subtilis, Agrobacterium tumefaciens, Bacillus megaterium*; and eukaryotic cells such as *Pichia pastoris, Chlamydomonas reinhardtii, Cryptococcus neoformans, Neurospora crassa, Podospora anserina, Saccharomyces cerevisiae, Saccharomyces pombe, Uncinula necator*, cultured insect cells, cultured chicken fibroblasts, cultured hamster cells, cultured human cells such as HT1080, MCF7, 143B and cultured mouse cells such as EL4 and NIH3T3 cells.

The present invention also provides a purified and isolated mycobacterial isocitrate lyase protein and analogues thereof, and includes mycobacterial isocitrate lyase protein isolated from nature and mycobacterial isocitrate lyase protein which is recombinantly produced. As used herein "analogues" may be any protein having the same action as isocitrate lyase.

The isocitrate lyase protein provided by the present invention may be isolated from any species of mycobacteria, including, but not limited to, *M. tuberculosis, M. smegmatis, M. avium, M. kansasii, M. zenopi, M. simiae, M. gastri, M. szulgai, M. gordonae, M. chelonea, M. leprae, M. bovis-BCG, M. intracellulare, M. habana, M. lufu, M. phlei, M. fortuitum, M. paratuberculosis* and *M. scrofulaceum*. In a preferred embodiment of the invention, the mycobacterial isocitrate lyase is isolated from *M. tuberculosis*. In another embodiment of the invention, mycobacterial isocitrate lyase is isolated from *M. smegmatis*.

In a preferred embodiment of the invention, the isocitrate lyase protein is *M. tuberculosis* isocitrate lyase and has the amino acid sequence containing in FIG. 1 (SEQ ID NO:2). In another embodiment of the invention, the isocitrate lyase protein is *M. smegmatis* isocitrate lyase and has the amino acid sequence containing in FIG. 2 (SEQ ID NO:4).

The present invention further provides for proteins encoded by mutated nucleic acids encoding mycobacterial isocitrate lyase. The mutation in the nucleic acid encoding the protein of the present invention may be generated in said nucleic acid using methods known to one of skill in the art. Such methods of mutation include, but are not limited to, signature-tagged mutagenesis, transposon mutagenesis, targeted gene disruption, illegitimate recombination and chemical mutagenesis. In a preferred embodiment of the invention, the isocitrate lyase protein is encoded by a mutated *M. tuberculosis* nucleic acid. In a more preferred embodiment on the invention, the mutation in the *M. tuberculosis* nucleic acid encoding isocitrate lyase is generated by disruption. Disruption of a nucleic acid encoding isocitrate lyase may be performed, for example, by allelic exchange. It is to be understood that the present invention also provides for nucleic acid sequences wherein any or all of the above described mutations coexist in the nucleic acid encoding mycobacterial isocitrate lyase in any combinations thereof.

The isocitrate protein of the present may also be encoded by a mutated nucleic acid sequence obtained from a library of mutants wherein the mutated mycobacteria are generated using methods of mutation which include, but are not limited to, signature-tagged mutagenesis, transposon mutagenesis, targeted gene disruption, illegitimate recombination and chemical mutagenesis. The disruption of a nucleic acid encoding isocitrate lyase may be performed, for example, by allelic exchange.

The isocitrate proteins and the amino acid sequences of these proteins may be isolated from mycobacteria such as *M. tuberculosis, M. smegmatis, M. avium, M. kansasii, M. zenopi, M. simiae, M. gastri, M. szulgai, M. gordonae, M. chelonea, M. leprae, M. bovis-BCG, M. intracellulare, M. habana, M. lufu, M. phlei, M. fortuitum, M. paratuberculosis* and *M. scrofulaceum*. The isocitrate proteins of the present invention and the amino acid sequences of these proteins also be synthesized by methods commonly known to one skilled in the art (*Modern Techniques of Peptide and Amino Acid Analysis*, John Wiley & Sons (1981); M. Bodansky, *Principles of Peptide Synthesis*, Springer Verlag (1984)). Examples of methods that may be employed in the synthesis of the amino acids sequences, and mutants of these sequences include, but are not limited to, solid phase peptide synthesis, solution method peptide synthesis, and synthesis using any of the commercially available peptide synthesizers. The amino acid sequences, and mutants thereof, may contain coupling agents and protecting groups used in the synthesis of the protein sequences, and are well known to one of skill in the art.

The present invention also provides a host cell transformed with a vector encoding mycobacterial isocitrate lyase. The introduction of the recombinant vector containing the DNA sequence into the cell may be effected by methods known to one skilled in the art, such as electroporation, DEAE Dextran, cationic liposome fusion, protoplast fusion, DNA coated microprojectile bombardment, injection with recombinant replication-defective viruses, homologous recombination, and naked DNA transfer. It will be appreciated by those skilled in the art that any of the above methods of DNA transfer may be combined.

The present invention also provides for antibodies immunoreactive with mycobacterial isocitrate lyase and analogues thereof. The antibodies of the present invention include antibodies immunoreactive with non-functional mycobacterial isocitrate lyase, i.e., isocitrate lyase which is inactive or exhibits only reduced activity in vivo. The non-functional isocitrate lyase recognized by the antibodies of the present invention may result from one or more mutations in the nucleic acid encoding mycobacterial isocitrate lyase or from one or more deficiencies in the cell s protein synthesis and maturation pathways which result in a mycobacterial isocitrate lyase with altered secondary or tertiary structure.

The antibodies of the present invention may be monoclonal or polyclonal and are produced by techniques well known to those skilled in the art, e.g., polyclonal antibody can be produced by immunizing a rabbit, mouse, or rat with purified mycobacterial isocitrate lyase and monoclonal antibody may be produced by removing the spleen from the immunized rabbit, mouse or rat and fusing the spleen cells with myeloma cells to form a hybridoma which, when grown in culture, will produce a monoclonal antibody. Labeling of the antibodies of the present invention may be accomplished by standard techniques using one of the variety of different chemiluminescent and radioactive labels known in the art. The antibodies of the present invention may also be incorporated into kits which include an appropriate labeling system, buffers and other necessary reagents for use in a variety of detection and diagnostic applications.

Further provided by the present invention is a mycobacterium that contains a mutation in its isocitrate lyase gene. The mycobacterium may be, for example, *M. tuberculosis, M. smegmatis, M. avium, M. kansasii, M. zenopi, M. simiae, M. gastri, M. szulgai, M. gordonae, M. chelonea, M. leprae, M. bovis*-BCG, *M. intracellulare, M. habana, M. lufu, M. phlei, M. fortuitum, M. paratuberculosis* or *M. scrofulaceum*.

The mutation may be generated in the isocitrate gene of the mycobacterium using methods known to one of skill in the art. Such methods of mutation include, but are not limited to, transposon mutagenesis, targeted gene disruption, illegitimate recombination and chemical mutagenesis. In a preferred embodiment of the invention, the mycobacterium is *M. tuberculosis*. In a more preferred embodiment of the invention, the mutation in the *M. tuberculosis* nucleic acid encoding isocitrate lyase is generated by disruption. Disruption of a nucleic acid encoding isocitrate lyase may be performed, for example, by allelic exchange. It is to be understood that the present invention also provides for nucleic acid sequences wherein any or all of the above described mutations coexist in the nucleic acid encoding mycobacterial isocitrate lyase in any combinations thereof.

The mycobacterium having a mutated isocitrate lyase gene provided by the present invention may also be obtained from a library of mutants wherein the mutated mycobacteria are generated using methods of mutation which include, but are not limited to, transposon mutagenesis, targeted gene disruption, illegitimate recombination and chemical mutagenesis. The disruption of a nucleic acid encoding isocitrate lyase may be performed, for example, by allelic exchange.

The present invention also provides an agent that inhibits the activity or expression of a mycobacterial lyase protein. The inventors have shown that the isocitrate lyase gene of *M. tuberculosis* is required for stationary-phase persistence of *M. tuberculosis*. Agents that inhibit the activity or expression of the mycobacterial lyase protein would specifically kill stationary phase *M. tuberculosis* in vivo. By attacking stationary phase 'persisters', an isocitrate lyase inhibitor could significantly accelerate the eradication of infection with chemotherapy.

Further provided by the present invention is a method of producing a compound that inhibits isocitrate lyase activity comprising: (a) providing purified isocitrate lyase; (b) determining the molecular structure of said isocitrate lyase; (c) locating the binding sites of said isocitrate lyase; (d) creating a compound with a similar structure to a binding site; (e) determining that said compound inhibits the biochemical activity of isocitrate lyase. The design and synthesis of an isocitrate lyase inhibitor should be relatively simple for two reasons: 1) the enzyme is a small protein of just 428 amino acids; 2) the ICL substrate (isocitrate) is a small molecule of known molecular structure. Isocitrate lyase is a particularly attractive target for rational drug design because this enzyme is not found in human cells; therefore, an isocitrate lyase inhibitor would not be expected to display toxicity for human cells. Because the isocitrate lyase substrate is a small molecule, a specific inhibitor might be obtained by high-throughput screening of a small-molecule library using purified isocitrate lyase enzyme. This approach would be facilitated by the fact that a simple in vitro assay for isocitrate lyase activity already exists. Alternatively, structure-based rational design of an isocitrate lyase inhibitor would ideally proceed by the following steps: 1) The *M. tuberculosis* enzyme isocitrate lyase would be overproduced in *Escherichia coli* and purified; 2) The 3-dimensional structure of the purified isocitrate lyase protein bound to its substrate (isocitrate) would be obtained by X-ray crystallography; 3) knowledge of the 3-dimensional co-crystal structure would permit chemical modifications of the substrate to be made in such a way that the modified substrate would act as a 'pseudo-substrate'. Binding of the 'pseudo-substrate' to the isocitrate lyase enzyme would sterically hinder binding of the bona fide substrate (isocitrate) and would therefore inhibit isocitrate lyase function. It might also be possible to design isocitrate lyase inhibitors that would become covalently linked to the isocitrate lyase enzyme, resulting in irreversible inhibition.

Also provided by the present invention is a method of determining whether a drug is effective against *Mycobacterium tuberculosis* comprising (a) providing isolated isocitrate lyase; (b) providing a candidate drug; (c) mixing isocitrate lyase with substrates the glyoxylate shunt in the presence or absence of the candidate drug; and (d) measuring any inhibition of biosynthesis of malate caused by the presence of the drug.

Further provided by the present invention is a method for treating or preventing tuberculosis in a subject comprising administering an effective amount of an agent that inhibits the activity or expression of mycobacterial isocitrate lyase protein to treat the tuberculosis.

Finally, the present invention provides a method of identifying a gene required for persistence of *Mycobacteria tuberculosis* in a subject comprising: (a) obtaining a library of *M. tuberculosis* mutants; (b) screening said library for an inactivated gene; (c) infecting a mammal with *M. tuberculosis* containing the inactivated gene; (d) determining whether there is persistence of the *M. tuberculosis* containing the inactivated gene in said mammal, said absence of persistence indicating that the inactive gene is necessary for persistence of *M. tuberculosis.*

Examples of mycobacterial genes which may be analyzed using this method of identifying genes required for persistence include, but are not limited to, the malate synthase gene, and genes involved in fatty acid catabolism.

The mutation in the mycobacterial gene may be generated using methods known to one of skill in the art. Such methods of mutation include, but are not limited to, signature-tagged mutations, transposon mutagenesis, targeted gene disruption, illegitimate recombination and chemical mutagenesis. In a preferred embodiment of the invention, the mycobacterium is *M. Tuberculosis*. In a more preferred embodiment of the invention, the mutation in *M. Tuberculosis* is in the isocitrate lyase gene, and is mutated by disruption. Disruption of an *M. Tuberculosis* gene may be performed, for example, by allelic exchange.

The mycobacterial library containing the mutations is then screened using a phenotypic analysis.

The present invention is described in the following Experimental Details Section which is set forth to aid in the understanding of the invention, and should not be construed to limit in any way the invention as defined in the claims which follow thereafter.

Experimental Details Section

I. Materials and Methods

Mycobacterial strains and growth conditions. $mc^2155$ is an "efficient plasmid transformation" (ept) mutant of *Mycobacterium smegmatis* (Snapper et al., 1990). Virulent *Mycobacterium tuberculosis* strain Erdman (Trudeau Institute, saranac Lake, N.Y.) was passaged through mice, grown once in culture, washed twice with phosphate buffered saline containing 0.1% Tween-80 and 10% glycerol, and stored in aliquots at 80° C.

Liquid growth medium was Middlebrook 7H9 broth (4.7 g/L 7H9 broth (DifCo), 0.2% dextrose, 0.5% glycerol, 0.5% bovine serum albumin (BSA) Fraction V (Boehringer Mannheim Biochemicals), 15 mM NaCl, 0.1% Tween-80). Solid growth medium for *M. smegmatis* was Middlebrook 7H10 agar (19 g/L 7H10 agar (DifCo), 0.2% dextrose, 0.5% glycerol, 0.5% BSA, 15 mM NaCl). Solid growth medium for *M. tuberculosis* was Middlebrook 7H10 oleic acid agar (19 g/L 7H10 agar (DifCo), 0.5% glycerol, 10% Middlebrook OADC Enrichment (BBL)). For analysis of *M. smegmatis* growth on alternative carbon sources, solid growth medium was Mycobacterial Basal (MB) medium (1.5% Bacto agar (DifCo), 0.5 mM $CaCl_2$, 0.5 mM $MgCl_2$, 0.1% $KH_2PO_4$, 0.25% $Na_2HPO_4$, 0.5% $NH_4Cl$, 0.2% $K_2SO_4$, 0.08 mg/L $ZnCl_2$, 0.4 mg/L $FeCl_3.6H_2O$, 0.02 mg/L $CuCl_2.2H_2O$, 0.02 mg/L $MnCl_2.4H_2O$, 0.02 mg/L $Na_2B_4O_7.10H_2O$, 0.02 mg/L $(NH_4)6Mo_7O24.4H_2O$) supplemented with either 0.5% glucose or 0.5% sodium acetate. For growth of *M. tuberculosis*, MB medium was supplemented with 0.5% BSA. Inclusion of BSA alone did not support growth of *M. tuberculosis* in the absence of an added carbon source (data not shown). All mycobacterial media contained 100 μg/mL cycloheximide to prevent fungal contamination. Where noted, 50 μg/mL hygromycin (Boehringer Mannheim Biochemicals) or 30 μg/mL kanamycin (Sigma) was included.

For assessment of survival during anaerobiosis, 3.5 liter DifCo anaerobic jars and anaerobic system envelopes were used as per the manufacturer's instructions. Mycobacteria were pre-adapted to anaerobiosis essentially as described previously (Wayne, 1982). Briefly, mycobacterial cells were inoculated into Middlebrook 7H9 broth at approximately $1\times10^8$ CFU per mL, aliquoted in 15 mL plastic screwcap tubes (Corning), and incubated at 37° C. upright without agitation for 6 weeks before use.

Ethyl Methane Sulfonate (EMS) mutagenesis. *M. smegmatis* strain $mc^2155$ bacilli were grown to mid-log phase (A600 0.5–1.0) in Middlebrook 7H9 broth and harvested by centrifugation. Cells were washed twice and resuspended in an equal volume of 0.1 M phosphate buffer (pH 7.0) containing 0.1% Tween-80. Ethyl methane sulfonate (EMS) (Sigma) was added to 2.5% and cells were incubated at 37° C. for 75–90 minutes, resulting in ~25% cell survival. Mutagenesis was terminated by the addition of thiosulfate (Sigma) to 4%. Cells were washed once with 4% thiosulfate containing 0.1% Tween-80, washed twice with Middlebrook 7H9 broth, and resuspended in Middlebrook 7H9 broth. After 3 hours' recovery at 37° C., the mutagenized cell suspension was sonicated and passed through a 5.0 micron pore syringe-filter (Micron Separations, Inc.) to remove clumps. Filtered cells were diluted and plated on Middlebrook 7H10 agar supplemented with 5 g/L Casamino acids (Sigma), 0.1 g/L DL-a,e-diaminopimelic acid (DAP) (Sigma), and 0.02 g/L tryptophan (Sigma) to permit recovery of amino acid auxotrophs. Colonies were patched to fresh plates to form an ordered collection of mutants and screened for the presence of auxotrophs to assess the complexity of the mutant bank. Out of 6000 individual colonies analyzed, 136 amino acid auxotrophs were recovered (frequency 2.3%), representing most of the classes of mutants expected.

Isolation and complementation of $Ace^-$ mutants of *M. smegmatis*. The EMS mutant bank was screened for isolates unable to grow on MB medium containing acetate as sole carbon source ($Ace^-$ phenotype). Eleven $Ace^-$ mutants were recovered from 3000 picks screened (frequency 0.37%). To identify potential isocitrate lyase (icl) mutants among these, each of the eleven $Ace^-$ mutants was transformed with a plasmid expressing the *Escherichia coli* icl gene from the mycobacterial hsp60 heat shock promoter (pJM007, see "Plasmids") and screened for growth on MB+acetate medium. Two of the eleven $Ace^-$ mutants (ACE1023 and ACE2832) were complemented by *E. coli* icl (frequency 0.067%).

The mycobacterial icl genes were isolated from cosmid libraries consisting of large (20–40 kbp) fragments of genomic DNA from *M. smegmatis* or *M. tuberculosis* inserted into the cosmid vector pYUB412. pYUB412 is an *E.coli*-Mycobacterium shuttle vector containing the oriE replication origin for maintenance in *E. coli*, the mycobacteriophage L5 attachment/integration system for site-specific insertion into the mycobacterial genome (Lee et al. 1991), the hygromycin phosphotransferase gene conferring hygromycin resistance in mycobacteria, the b-lactamase gene conferring ampicillin resistance in *E. coli*, and dual cos sites for packaging in phage 1 heads. The pYUB412 polylinker is flanked by recognition sites for restriction endonuclease PacI (New England Biolabs), which has few or no recognition sites in mycobacterial genomic DNA; digestion with PacI therefore releases the intact genomic insert. Construction of the mycobacterial genomic libraries (generously provided to us by F.-C. Bange) will be described elsewhere. The libraries were electroporated into the Ace⁻ strain ACE1023 and Ace+ transformants were selected on MB+acetate medium.

Integrated cosmid inserts were recovered from the mycobacterial genomic DNA as follows. pYUB412 cosmid arms were prepared by digestion with XbaI (New England Biolabs) to separate cos sites, dephosphorylation with calf intestinal phosphatase (Boehringer Mannheim Biochemicals) to prevent self-ligation, and digestion with PacI. Genomic DNA was prepared from individual Ace+ transformants as described (Mizuguchi and Tokunaga 1970) and digested with PacI. pYUB412 cosmid arms and PacI-digested genomic DNA were ligated (DNA ligase from Boehringer Mannheim Biochemicals), packaged into phage l heads using GigaPack Gold (Stratagene) packaging mix, and transduced into $E.\ coli$ strain STBL2 (Stratagene), all according to the manufacturers' instructions. Transductants were selected on LB medium containing 50 $\mu$g/mL ampicillin. Plasmid DNA was isolated from individual transductants using standard methods and electroporated into ACE1023. Transformants were selected on Middlebrook 7H10 agar containing 50 $\mu$g/mL hygromycin and screened for the ability to grow on MB+dextrose and MB+acetate.

Southern blot analysis. Genomic and plasmid DNAs were digested with restriction endonucleases (New England Biolabs) as indicated in the text and separated on 1.0% agarose-TBE gels. Gels were processed and transferred to Hybond-N+ nylon membranes (Amersham) as per the manufacturer's instructions. The $M.\ tuberculosis$ icl probe fragment was prepared by polymerase chain reaction (PCR) amplification of a 981 bp SacII fragment subcloned into the vector pKS+ (Stratagene), using T3 and T7 oligonucleotides flanking the polylinker site and Vent polymerase (New England Biolabs). The amplified fragment was labeled using the Enhanced Chemiluminescence kit (Amersham) and the blot was probed and developed according to the manufacturer's instructions.

Analysis of mycobacterial growth and persistence in mice. Male C57BL/6J mice were obtained from Jackson Laboratories (Bar Harbor, Me.). Female 129SvEv mice were obtained from Taconic (Germantown, N.Y.). The B6X129 F1 progeny of the C57BL/6J×129SvEv cross were used for experiments. Frozen stocks of wild-type (icl+) and icl⁻ $M.\ tuberculosis$ strain Erdman were prepared by growing cells to mid-log phase (A600 0.5–1.0) in Middlebrook 7H9 broth, washing cells twice with phosphate-buffered saline containing 0.1% Tween-80 and 10% glycerol, and storing in aliquots at/–80° C. Aliquots were thawed, diluted as appropriate in phosphate-buffered saline containing 0.1% Tween-80, and sonicated in two 10 sec bursts using a cup-horn sonicator. Mice were infected intravenously by injection into a lateral tail vein of approximately $1 \times 10^6$ CFU of tubercle bacilli in a volume of 0.1 mL.

At timepoints indicated in the text, mice (four per group) were sacrificed by cervical dislocation and organs were removed aseptically. Organs were transferred to plastic Stomacher bags (Tekmar, Cincinnati, Ohio) with phosphate buffered saline containing 0.1% Tween-80 and homogenized using a Stomacher homogenizer (Tekmar). Organ homogenates were diluted in phosphate buffered saline containing 0.1% Tween-80 and plated on Middlebrook 7H10 oleic acid agar. Colonies were scored after 3–4 weeks' incubation at 37° C.

II. Results

The Krebs cycle serves dual functions in metabolism: generation of metabolic energy by oxidation of acetyl CoA, and provision of intermediates for several essential biosynthetic pathways. Sustained operation of the Krebs cycle therefore requires an anaplerotic function to replenish intermediates that are siphoned off for biosyntheses. Pyruvate carboxylase satisfies this requirement for cells growing on carbohydrates. This pathway is not operative when cells are grown on C2 carbon sources such as acetate or fatty acids, since carbon from these substrates enters metabolism at the level of acetyl CoA. Instead, a novel anaplerotic pathway, the glyoxylate shunt, is induced during growth on C2 substrates. The glyoxylate shunt consists of two enzymes, isocitrate lyase and malate synthase, which catalyze the formation of one molecule of malate (a Krebs cycle intermediate) from two molecules of acetyl CoA. Synthesis of these enzymes is repressed during growth on carbohydrates. The glyoxylate shunt is present in many eubacterial species and in some simple eukaryotes (including fungi) but is absent in vertebrates.

Metabolic studies of tubercle bacilli purified directly from the lungs of chronically infected mice suggested that fatty acids may serve as an important source of carbon and energy for mycobacteria within the infected host. If so, then the fatty acid b-oxidation pathway and the glyoxylate shunt may be essential for in vivo growth or persistence. The inventors have begun to address this hypothesis using newly-developed molecular genetic techniques for the generation of targeted mutations in mycobacteria, focusing first on the enzymes of the glyoxylate shunt. Here, we describe the isolation of the genes encoding isocitrate lyase in fast- and slow-growing mycobacteria, targeted disruption of the icl locus in virulent $M.\ tuberculosis$, and phenotypic analysis of the $M.\ tuberculosis$ icl mutant.

Isolation of Ace mutants of $Mycobacterium\ smegmatis$. In order to identify functions required for utilization of $C_2$ carbon sources in mycobacteria, a genetic screen was conducted in the fast-growing species $Mycobacterium\ smegmatis$. A library of mutant clones was generated by mutagenesis with ethane methyl sulfonate (EMS), as described in Materials and Methods. From a collection of 3000 mutant clones, 11 mutants (frequency 0.37%) were identified that were incapable of growth on acetate as sole carbon source (Ace⁻ phenotype). To identify potential isocitrate lyase (icl) mutants, the 11 Ace mutants were transformed with an $E.\ coli$-Mycobacterium shuttle plasmid expressing the $E.\ coli$ icl gene from the mycobacterial hsp60 promoter. Growth of two of the 11 Ace mutants on acetate (frequency 0.067%) was restored by expression of $E.\ coli$ icl. One of these mutants (ACE 1023) displayed a tight Ace-phenotype (FIGS. 3A, 3E) and a low reversion rate ($<10^{-7}$; data not shown) and was selected for further analysis.

Complementation of a putative icl mutant of $M.\ smegmatis$ with genomic libraries of $M.\ smegmatis$ and $M.\ tuberculosis$. The ACE 1023 mutant of $M.\ smegmatis$ was transformed with genomic cosmid libraries containing inserts of $M.\ smegmatis$ or $M.\ tuberculosis$ genomic DNA. These libraries were constructed in the shuttle vector pYUB412, which utilizes the mycobacteriophage L5 attachment/integration system for single-copy insertion into the attB site of the mycobacterial chromosome. Transformants were selected on 7H10+AD medium containing 50 $\mu$g/mL hygromycin and screened for complementation of the Ace phenotype. Growth on acetate was restored in approximately 1 of 250 transformants obtained with the $M.\ smegmatis$ library and in approximately 1 of 200 transformants obtained with the *M. tuberculosis* library. In order to ensure that growth on acetate resulted from expression of the complementing clone and not from reversion of the mutation, the integrated plasmid inserts were retrieved (see Materials and Methods) and retransformed into the ACE 1023 strain. Twelve independent clones from the *M. smegmatis* library and 11 independent clones from the *M. tuberculosis* library were analyzed; all restored growth on acetate when retransformed into ACE 1023. One clone from each library was arbitrarily selected for further analysis. These cosmid clones contained inserts of 20–40 kbp. By a combination of subcloning and complementation analysis, smaller complementing fragments were obtained: a 2558 base-pair HpaI-EcoRI genomic fragment from *M. smegmatis* and a 2674 base-pair BamHI-ClaI genomic fragment from *M. tuberculosis* (FIGS. 4B and 4A respectively).

Nucleotide sequence and Southern blot analysis of the *M. smegmatis* and *M. tuberculosis* genes encoding isocitrate lyase (ICL). The nucleotide sequences of the putative icl loci from *M. smegmatis* and *M. tuberculosis* (see previous section) were determined and potential open reading frames (ORFs) were identified. Each fragment contained an ORF encoding a conceptual protein homologous to the isocitrate lyase proteins of other gram-positive and gram-negative organisms. The conceptual ICL proteins from *M. smegmatis* and *M. tuberculosis* are 92% identical to each other and both are ~84% identical to the ICL protein from *Rhodococcus fasciens* (FIG. 5).

Figure 4A:
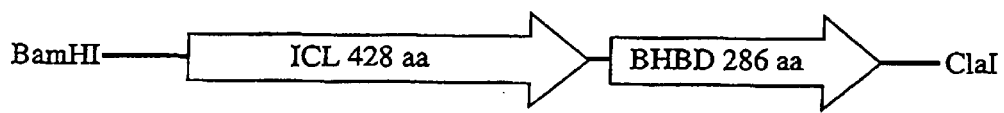
FIG. 4A sets forth a diagram indicating the position of the gene encoding 3-hydroxybutyryl-CoA dehydrogenase in relation to the isocitrate lyase gene in M. tuberculosis.
Figure 4B:
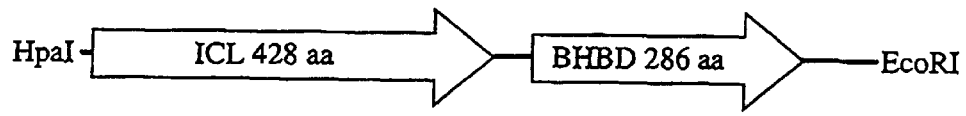
FIG. 4B sets forth a diagram indicating the position of the gene encoding 3-hydroxybutyryl-CoA dehydrogenase in relation to the isocitrate lyase gene in M. smegmatis.

Situated just downstream of the icl genes in both *M. smegmatis* and *M. tuberculosis* are ORFs with significant homology to genes encoding 3-hydroxybutyryl-CoA dehydrogenase (BHBD) in other eubacterial species (FIGS. 4B and 4A respectively). The putative BHBD proteins encoded by *M. smegmatis* and *M. tuberculosis* are 83% identical to each other and both are ~45% identical to the BHBD protein from *Clostridium acetobutylicum*. In the latter species, BHBD catalyzes the conversion of acetoacetyl-CoA to 3-hydroxybutyryl-CoA in the butyrate/butanol fermentation pathway for generation of ATP and regeneration of oxidized NAD+ during anaerobic growth. Mycobacteria, however, are obligate aerobes and are not capable of growing anaerobically by fermentation. The possible significance of a BHBD homolog in mycobacteria will be discussed later.

The identity of the cloned icl genes was confirmed by Southern blot analysis of *M. smegmatis* and *M. tuberculosis* genomic DNAs using fragments derived from the cloned icl genes as probes.

Figure 6A:
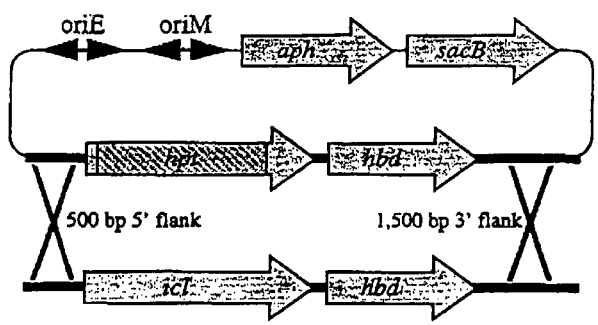
FIG. 6A sets forth a diagram showing the targeted disruption of the isocitrate lyase gene in M. tuberculosis.

Targeted disruption of the isocitrate lyase gene in virulent *M. tuberculosis*. The icl gene was disrupted in the virulent Erdman strain of *M. tuberculosis* using an efficient method for allelic exchange. This method employs the counter-selectable marker sacB, which is lethal in the presence of sucrose. Successful application of sacB for efficient allelic exchange in *M. tuberculosis* was described recently by Pelicic et al. (1997). A 685 base-pair XhoI fragment internal to the *M. tuberculosis* icl gene was replaced with the hygromycin phosphotransferase (hpt) gene from *Streptomyces hygroscopicus* (FIG. 6A). The recombinant icl::hpt allele was incapable of rescuing growth of the ACE 1023 mutant on acetate, confirming that the disrupted gene was not functional (data not shown). The icl::hpt cassette was inserted into the shuttle vector pMP7, which contains the oriE and oriM replication origins for plasmid maintenance in *E. coli* and mycobacteria (respectively), the aph gene conferring kanamycin resistance, and the counter-selectable sacB marker from *Bacillus subtilis*. The resulting plasmid (pJM056) was electroporated into *M. tuberculosis* strain Erdman MC²3030 and transformants were selected on solid medium containing 50 µg/mL hygromycin. MC²3030, containing the icl::hpt recombinant allele has been deposited under the terms of the Budapest Treaty on Apr. 3, 1998 with the American Type Culture Collection (ATCC), located at 10801 University Boulevard, Manassas, Va. 20110-2209, and assigned ATCC Accession No. 202104. In the absence of antibiotic selection, the plasmid was rapidly lost in broth cultures (data not shown). Therefore, transformants grown in the presence of hygromycin were expected to lose the plasmid following allelic exchange between the chromsomal icl gene and the icl::hpt allele on the plasmid.

Figure 6B:
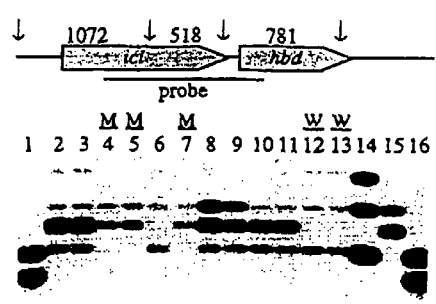
FIG. 6B sets forth the results of a Southern blot analysis of mutants generated by the targeted disruption.

Five individual colonies obtained from independent transformations with pJM056 were picked, inoculated separately into liquid medium containing 50 µg/mL hygromycin, and grown to saturation to allow time for recombination to occur between the plasmid and the bacterial chromosome. The saturated broth cultures were diluted and plated on solid medium containing 50 µg/mL hygromycin +/−5% sucrose. Expression of sacB in *M. tuberculosis* was lethal on solid medium containing 5% sucrose, permitting selection against cells that retained the pMP7 vector. The relative plating efficiencies of the individual broth cultures on medium plus/minus sucrose were variable ($10^0$ to $10^{-3}$), suggesting that loss of sacB function occurred at different times in the growth of the cultures. Twenty-five hgmr sucr colonies derived from each liquid culture were screened for the ability to grow on kanamycin. Two of five cultures yielded colonies that were uniformly (25/25) resistant to kanamycin; these presumably carried mutations in sacB and were discarded. The three remaining cultures yielded hgmr sucr colonies that were sensitive (25/25) to kanamycin. From each of these cultures, individual hgmr sucr kans colonies were expanded and analyzed by Southern blot (FIG. 6B). Of the 10 colonies analyzed, three colonies obtained from two independent cultures contained only the disrupted icl::hpt allele, establishing that allelic exchange had occurred (FIG. 6B).

Figure 7A:
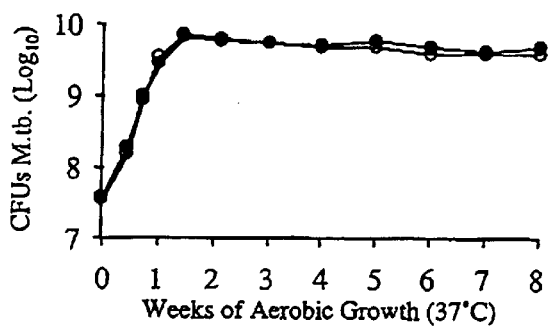
FIG. 7A sets forth a graph depicting the growth of an M. tuberculosis isocitrate lyase mutant.

Phenotypic analysis of the *M. tuberculosis* isocitrate lyase mutant. As expected, disruption of icl abrogated growth on solid medium containing acetate as sole carbon source (data not shown). In contrast, growth of the *M. tuberculosis* icl mutant was normal when glucose and glycerol were provided as carbon sources (FIG. 7A). Suryanarayana et al. (1973) demonstrated that ICL levels increased during entry of *M. tuberculosis* into stationary phase, suggesting that the glyoxylate shunt might play a role in stasis survival. They postulated that endogenous fatty acids might serve as an alternative carbon source for maintenance metabolism following depletion of exogenous carbon sources. However, we found that the ability of the icl mutant to survive long-term stasis was unimpaired (FIG. 7A).

Figure 7B:
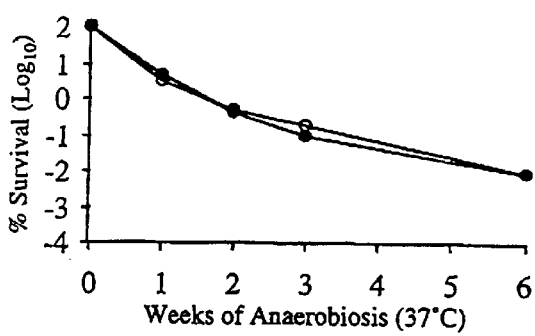
FIG. 7B sets forth a graph depicting the percent survival of an M. tuberculosis isocitrate lyase mutant.

Wayne and Lin (1982) found that ICL levels increased during adaptation of tubercle bacilli to anaerobiosis. They proposed the existence of a novel pathway involving ICL and another enzyme, glycine dehydrogenase, for the regeneration of NAD+ from NADH at oxygen tensions too low to support respiration. However, the demonstration that survival of oxygen starvation was not impaired by disruption of icl (FIG. 7B) suggests that this pathway, if it exists, is not essential for adaptation to anaerobiosis.

Figure 8A:
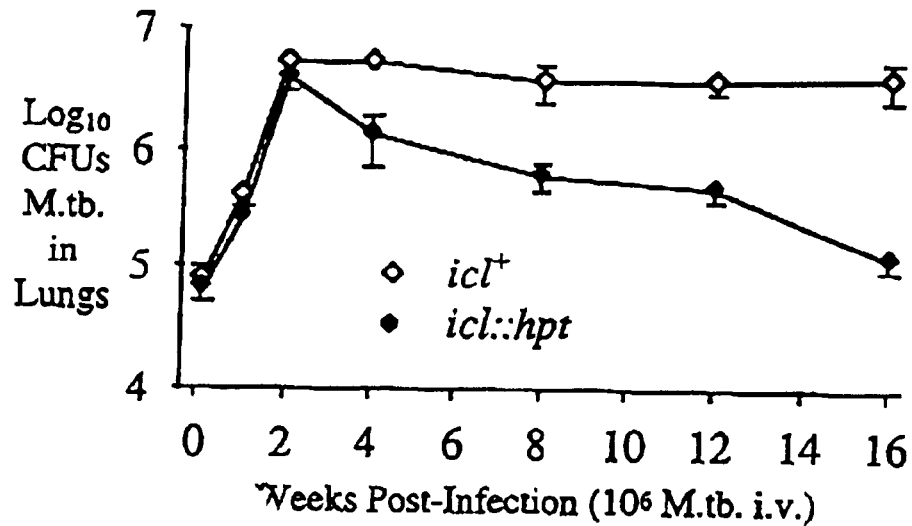
FIG. 8A sets forth a graph depicting the ability of an M. tuberculosis isocitrate lyase mutant to grow and persist in a mouse model.
Figure 8B:
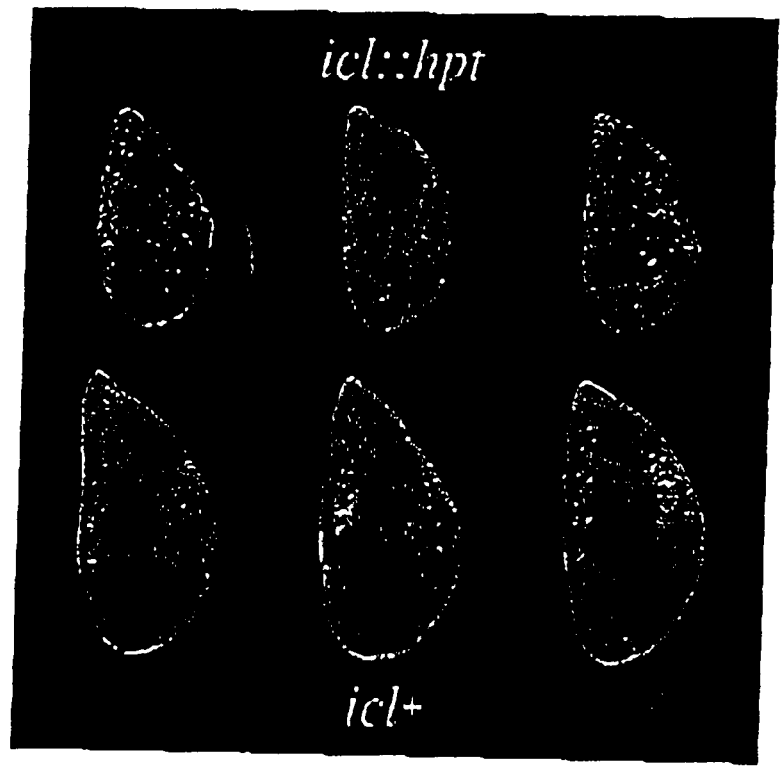
FIG. 8B indicates that persistence of the M. tuberculosis isocitrate lyase mutant in infected mice was impaired.

The aim of the studies described herein was to determine whether the glyoxylate shunt is important for in vivo nutrition of tubercle bacilli. The ability of the *M. tuberculosis* icl mutant to grow and persist in the mouse model of tuberculosis was therefore assessed. Mice were infected by the intravenous route with approximately $2 \times 10^6$ colony-forming units (CFU) of either wild-type (icl+) *M. tuberculosis* or the icl-mutant. Bacterial loads in the lungs were determined at 1 day and at 1, 2, 4, 8, 12, and 16 weeks post-infection (FIG. 8A). In the early phase of infection (up to 2 weeks), prior to the emergence of adaptive immunity (Orme, 1994), in vivo growth of the icl- and wild-type (icl+) bacilli was similar. Following the emergence of bacteriostatic immunity after 2 weeks, growth of wild-type *M. tuberculosis* ceased and a constant bacterial load was maintained thereafter. In contrast, from 2 weeks onwards, the titer of the icl mutant in the lungs fell steadily, resulting in a 40-fold reduction in the bacterial burden by 16 weeks post-infection. These results demonstrate that isocitrate lyase is not required for early growth of *M. tuberculosis* prior to the emergence of bacteriostatic immunity, but is important for chronic persistence once growth ceases. The "persistence defect" of the icl mutant resulted in a striking attenuation of disease progression (FIG. 8B).

III. Discussion

It is a truism that *M. tuberculosis* must acquire nutrients from the infected host in order to replicate and cause disease. Little is known, however, of the mechanisms that are involved in nutrient acquisition in vivo. A number of potential sources of carbon and energy are abundant in mammalian cells, but it is not known which of these substrates are available to mycobacteria growing within the confines of tightly-apposed vacuolar membranes. Tuberele bacilli may modify the vacuolar membrane in order to gain access to the rich variety of substrates that are abundant in the cytoplasm of the host cell. However, the inability of a leucine auixotroph of *M. bovis* BCG to replicate within macrophages suggests that access to cytoplasmic constituents may be limited. One substrate that would be readily accessible to mycobacteria growing within the parasitophorous vacuole is the fatty acids of the vacuolar membrane itself. In mammalian cells, fatty acids are potentially one of the most abundant carbon substrates available (Wheeler and Ratledge, 1994). *M. tuberculosis* produces a number of lipases and phospholipases capable of liberating free fatty acids from membrane-associated and storage forms such as phospholipids and triglycerides. Continuous fusion of the mycobacterium-containing vacuole with host-derived vesicles could serve to replenish membrane consumed by the parasite. *M. tuberculosis* also encodes the molecular machinery required for utilization of fatty acids as sole carbon source: the b-oxidation pathway for breakdown of fatty acids to assimilable acetyl-CoA units, and the glyoxylate shunt required for replenishment of Krebs cycle intermediates depleted by biosynthetic pathways. The enzymes of both pathways are expressed by pathogenic mycobacteria growing in vivo. Metabolic studies of in vivo grown mycobacteria also suggested that fatty acids may serve as a major source of carbon and energy during growth within the infected host.

SEQUENCE LISTING

<160> NUMBER OF SEQ ID NOS: 5

<210> SEQ ID NO 1
<211> LENGTH: 1287
<212> TYPE: DNA
<213> ORGANISM: Mycobacterium smegmatis
<220> FEATURE:
<221> NAME/KEY: gene
<222> LOCATION: (1)..(1285)

<400> SEQUENCE: 1

```
atgtctgtcg tcggcacccc gaagagcgcg gagcagatcc agcaggaatg ggacacgaac        60
ccgcgctgga aggacgtcac ccgcacctac tccgccgagg acgtcgtcgc cctccagggc       120
agcgtggtcg aggagcacac gctggcccgc cgcggtgcgg aggtgctgtg ggagcagctg       180
cacgacctcg agtgggtcaa cgcgctgggc gcgctgaccg gcaacatggc cgtccagcag       240
gtgcgcgccg gcctgaaggc catctacctg tcgggctggc aggtcgccgg cgatgccaac       300
ctgtccgggc acacctaccc cgaccagagc ctgtatcccg ccaactcggt gccgcaggtg       360
gtccgccgga tcaacaacgc actgcagcgc gccgaccaga tcgccaagat cgagggcgat       420
acttcggtgg agaactggct ggcgccgatt gtcgccgacg gcgaggccgg ctttggcggc       480
gcgctcaacg tctacgagct gcagaaagcc ctgatcgccg cgggcgttgc gggttcgcac       540
tgggaggacc agttggcctc tgagaagaag tgcggccacc tgggcggcaa ggtgttgatc       600
ccgacccagc agcacatccg cactttgacg tctgctcggc tcgcggccga tgtggctgat       660
gttcccacgg tggtgatcgc ccgtaccgac gccgaggcgg ccacgctgat cacctccgac       720
gtcgacgagc gcgaccagcc gttcatcacc ggcgagcgca cccgggaagg cttctaccgc       780
accaagaacg gcatcgagcc ttgcatcgct cgggcgaagg cctacgcccc gttcgccgac       840
ttgatctgga tggagaccgg taccccggac ctcgaggccg cccggcagtt ctccgaggcg       900
```

```
gtcaaggcgg agtacccgga ccagatgctg gcctacaact gctcgccatc gttcaactgg      960
aaaaagcacc tcgacgacgc caccatcgcc aagttccaga aggagctggc agccatgggc     1020
ttcaagttcc agttcatcac gctggccggc ttccatgcgc tgaactactc gatgttcgat     1080
ctggcctacg gctacgccca gaaccagatg agcgcgtatg tcgaactgca ggaacgcgag     1140
ttcgccgccg aagaacgggg ctacaccgcg accaagcacc agcgcgaggt cggcgccggc     1200
tacttcgacc ggattgccac caccgtggac ccgaattcgt cgaccaccgc gttgaccggt     1260
tccaccgaag agggccagtt ccactag                                         1287
```

<210> SEQ ID NO 2
<211> LENGTH: 428
<212> TYPE: PRT
<213> ORGANISM: Mycobacterium tuberculosis

<400> SEQUENCE: 2

```
Met Ser Val Val Gly Thr Pro Lys Ser Ala Glu Gln Ile Gln Gln Glu
 1               5                  10                  15

Trp Asp Thr Asn Pro Arg Trp Lys Asp Val Thr Arg Thr Tyr Ser Ala
                20                  25                  30

Glu Asp Val Val Ala Leu Gln Gly Ser Val Val Glu Glu His Thr Leu
            35                  40                  45

Ala Arg Arg Gly Ala Glu Val Leu Trp Glu Gln Leu His Asp Leu Glu
        50                  55                  60

Trp Val Asn Ala Leu Gly Ala Leu Thr Gly Asn Met Ala Val Gln Gln
    65                  70                  75                  80

Val Arg Ala Gly Leu Lys Ala Ile Tyr Leu Ser Gly Trp Gln Val Ala
                85                  90                  95

Gly Asp Ala Asn Leu Ser Gly His Thr Tyr Pro Asp Gln Ser Leu Tyr
            100                 105                 110

Pro Ala Asn Ser Val Pro Gln Val Val Arg Arg Ile Asn Asn Ala Leu
        115                 120                 125

Gln Arg Ala Asp Gln Ile Ala Lys Ile Glu Gly Asp Thr Ser Val Glu
    130                 135                 140

Asn Trp Leu Ala Pro Ile Val Ala Asp Gly Glu Ala Gly Phe Gly Gly
145                 150                 155                 160

Ala Leu Asn Val Tyr Glu Leu Gln Lys Ala Leu Ile Ala Ala Gly Val
                165                 170                 175

Ala Gly Ser His Trp Glu Asp Gln Leu Ala Ser Glu Lys Lys Cys Gly
            180                 185                 190

His Leu Gly Gly Lys Val Leu Ile Pro Thr Gln Gln His Ile Arg Thr
        195                 200                 205

Leu Thr Ser Ala Arg Leu Ala Ala Asp Val Ala Asp Val Pro Thr Val
    210                 215                 220

Val Ile Ala Arg Thr Asp Ala Glu Ala Ala Thr Leu Ile Thr Ser Asp
225                 230                 235                 240

Val Asp Glu Arg Asp Gln Pro Phe Ile Thr Gly Glu Arg Thr Arg Glu
                245                 250                 255

Gly Phe Tyr Arg Thr Lys Asn Gly Ile Glu Pro Cys Ile Ala Arg Ala
            260                 265                 270

Lys Ala Tyr Ala Pro Phe Ala Asp Leu Ile Trp Met Glu Thr Gly Thr
        275                 280                 285

Pro Asp Leu Glu Ala Ala Arg Gln Phe Ser Glu Ala Val Lys Ala Glu
    290                 295                 300
```

-continued

Tyr Pro Asp Gln Met Leu Ala Tyr Asn Cys Ser Pro Ser Phe Asn Trp
305                 310                 315                 320

Lys Lys His Leu Asp Asp Ala Thr Ile Ala Lys Phe Gln Lys Glu Leu
            325                 330                 335

Ala Ala Met Gly Phe Lys Phe Gln Phe Ile Thr Leu Ala Gly Phe His
            340                 345                 350

Ala Leu Asn Tyr Ser Met Phe Asp Leu Ala Tyr Gly Tyr Ala Gln Asn
            355                 360                 365

Gln Met Ser Ala Tyr Val Glu Leu Gln Glu Arg Glu Phe Ala Ala Glu
        370                 375                 380

Glu Arg Gly Tyr Thr Ala Thr Lys His Gln Arg Glu Val Gly Ala Gly
385                 390                 395                 400

Tyr Phe Asp Arg Ile Ala Thr Thr Val Asp Pro Asn Ser Ser Thr Thr
            405                 410                 415

Ala Leu Thr Gly Ser Thr Glu Glu Gly Gln Phe His
            420                 425

<210> SEQ ID NO 3
<211> LENGTH: 1287
<212> TYPE: DNA
<213> ORGANISM: Mycobacterium smegmatis
<220> FEATURE:
<221> NAME/KEY: gene
<222> LOCATION: (1)..(1287)

<400> SEQUENCE: 3
atgtcgaccg ttggcacccc gaagtccccc gagcagatcc agcacgactg ggatcacaac      60
ccccgctgga agggcatcaa gcgcgactac accccgagg acgtcgtggc cctgcagggc     120
accgtcgtcg aggagcacac cctggcccgc cgcggcgccg aggtgctgtg ggagcagctg     180
cacgacatgg acttcgtcaa cgcgctcggc gcgctgaccg caacatggc cgtccagcag     240 gttcgcgcgg gcctcaaggc catctacctg tccggctggc aggtcgccgg tgacgccaac     300
ctgtccggtc acacctaccc cgaccagagc ctgtacccgg ccaactcggt gccgcaggtg     360
gtccgccgca tcaacaacgc gctgctgcgc gccgacgaga tcgccaaggt cgagggcgac     420
acctcggtgg agaactggct ggctccgatc gtcgccgacg cgaggccgg cttcggtggt     480 gccctcaacg tctacgagct gcagaaggcg atgatcgccg cgggtgtcgc gggctcgcac     540
tgggaagatc agctggcctc ggagaagaag tgcggccacc tcgtggcaa ggtgctgatc     600 ccgacccagc agcacatccg caccctgacc tcggcgcgcc tggcggccga cgtggccgac     660
gtgcccaccg tcgtcatcgc ccgcaccgac gccgaggccg ccacgctgat cacgtccgac     720
gtcgacgagc gcgaccagcc gttcatcacc ggtgagcgca ccaaggaagg cttcttccgc     780
gtgaagaacg gcctggagcc ctgcatcgcg cgcgccaagg cctacgcgcc gtactccgac     840
ctgatctgga tggagaccgg cacgccggat ctcgagctcg ccaagaagtt cgccgagggc     900
gtcaaggcgg agttccccga ccagatgctg gcctacaact gctcgccgtc gttcaactgg     960
aagaagcacc tcgacgacgc caccatcgcg aagttccaga ggaactggg cgccatgggc    1020 ttcaagttcc agttcatcac gctggccggc ttccacgcgc tcaactactc gatgttcgat    1080
ctggcctacg gctacgcccg caaccagatg agcgcgtacg tcgaactgca ggagcgcgag    1140
ttcgctgccg aggagcgcgg ctacaccgcc accaagcacc agcgcgaggt gggtgccggc    1200
tacttcgacc gcatcgccac cacggtcgac cccaacagct cgaccaccgc gctcgcgggc    1260
tcgaccgaag agggtcagtt ccactga                                        1287

```
<210> SEQ ID NO 4
<211> LENGTH: 428
<212> TYPE: PRT
<213> ORGANISM: Mycobacterium smegmatis

<400> SEQUENCE: 4

Met Ser Thr Val Gly Thr Pro Lys Ser Pro Glu Gln Ile Gln His Asp
 1               5                  10                  15

Trp Asp His Asn Pro Arg Trp Lys Gly Ile Lys Arg Asp Tyr Thr Pro
            20                  25                  30

Glu Asp Val Val Ala Leu Gln Gly Thr Val Glu His Thr Leu
        35                  40                  45

Ala Arg Arg Gly Ala Glu Val Leu Trp Glu Gln Leu His Asp Met Asp
    50                  55                  60

Phe Val Asn Ala Leu Gly Ala Leu Thr Gly Asn Met Ala Val Gln Gln
65                  70                  75                  80

Val Arg Ala Gly Leu Lys Ala Ile Tyr Leu Ser Gly Trp Gln Val Ala
                85                  90                  95

Gly Asp Ala Asn Leu Ser Gly His Thr Tyr Pro Asp Gln Ser Leu Tyr
            100                 105                 110

Pro Ala Asn Ser Val Pro Gln Val Val Arg Arg Ile Asn Asn Ala Leu
        115                 120                 125

Leu Arg Ala Asp Glu Ile Ala Lys Val Glu Gly Asp Thr Ser Val Glu
    130                 135                 140

Asn Trp Leu Ala Pro Ile Val Ala Asp Gly Glu Ala Gly Phe Gly Gly
145                 150                 155                 160

Ala Leu Asn Val Tyr Glu Leu Gln Lys Ala Met Ile Ala Ala Gly Val
                165                 170                 175

Ala Gly Ser His Trp Glu Asp Gln Leu Ala Ser Glu Lys Lys Cys Gly
            180                 185                 190

His Leu Gly Gly Lys Val Leu Ile Pro Thr Gln Gln His Ile Arg Thr
        195                 200                 205

Leu Thr Ser Ala Arg Leu Ala Ala Asp Val Ala Asp Val Pro Thr Val
    210                 215                 220

Val Ile Ala Arg Thr Asp Ala Glu Ala Ala Thr Leu Ile Thr Ser Asp
225                 230                 235                 240

Val Asp Glu Arg Asp Gln Pro Phe Ile Thr Gly Glu Arg Thr Lys Glu
                245                 250                 255

Gly Phe Phe Arg Val Lys Asn Gly Leu Glu Pro Cys Ile Ala Arg Ala
            260                 265                 270

Lys Ala Tyr Ala Pro Tyr Ser Asp Leu Ile Trp Met Glu Thr Gly Thr
        275                 280                 285

Pro Asp Leu Glu Leu Ala Lys Lys Phe Ala Glu Gly Val Lys Ala Glu
    290                 295                 300

Phe Pro Asp Gln Met Leu Ala Tyr Asn Cys Ser Pro Ser Phe Asn Trp
305                 310                 315                 320

Lys Lys His Leu Asp Asp Ala Thr Ile Ala Lys Phe Gln Lys Glu Leu
                325                 330                 335

Gly Ala Met Gly Phe Lys Phe Gln Phe Ile Thr Leu Ala Gly Phe His
            340                 345                 350

Ala Leu Asn Tyr Ser Met Phe Asp Leu Ala Tyr Gly Tyr Ala Arg Asn
        355                 360                 365

Gln Met Ser Ala Tyr Val Glu Leu Gln Glu Arg Glu Phe Ala Ala Glu
```

```
            370                 375                 380
Glu Arg Gly Tyr Thr Ala Thr Lys His Gln Arg Glu Val Gly Ala Gly
385                 390                 395                 400

Tyr Phe Asp Arg Ile Ala Thr Val Asp Pro Asn Ser Ser Thr Thr
                405                 410                 415

Ala Leu Ala Gly Ser Thr Glu Glu Gly Gln Phe His
                420                 425

<210> SEQ ID NO 5
<211> LENGTH: 428
<212> TYPE: PRT
<213> ORGANISM: Rhodococcus fascians

<400> SEQUENCE: 5

Met Ser Thr Thr Gly Thr Pro Lys Thr Thr Ala Glu Ile Gln Gln Asp
  1               5                  10                  15

Trp Asp Thr Asn Pro Arg Trp Lys Gly Val Thr Arg Asn Phe Thr Ala
                 20                  25                  30

Gln Gln Val Ser Asp Leu Gln Gly Thr Val Val Glu Glu Ala Thr Leu
             35                  40                  45

Ala Arg Arg Gly Ser Glu Ile Leu Trp Asp Leu Val Asn Asn Glu Asp
         50                  55                  60

Tyr Ile Asn Ser Leu Gly Ala Leu Thr Gly Asn Gln Ala Val Gln Gln
 65                  70                  75                  80

Ile Arg Ala Gly Leu Gln Ala Ile Tyr Leu Ser Gly Trp Gln Val Ala
                 85                  90                  95

Gly Asp Ala Asn Leu Ser Gly His Thr Tyr Pro Asp Gln Ser Leu Tyr
            100                 105                 110

Pro Ala Asn Ser Val Pro Ser Val Val Arg Arg Ile Asn Asn Ala Leu
        115                 120                 125

Leu Arg Ala Asp Glu Ile Ala Lys Ile Glu Gly Asp Thr Ser Val Lys
130                 135                 140

Asn Trp Val Ala Pro Ile Val Ala Asp Ala Glu Ala Gly Phe Gly Gly
145                 150                 155                 160

Ala Leu Asn Ala Tyr Glu Leu Gln Lys Ala Met Ile Val Ala Gly Ala
                165                 170                 175

Ala Gly Val His Trp Glu Asp Gln Leu Ala Ser Glu Lys Lys Cys Gly
            180                 185                 190

His Leu Gly Gly Lys Val Leu Ile Pro Thr Gln Gln His Ile Arg Thr
        195                 200                 205

Leu Thr Ser Ala Arg Leu Ala Ser Asp Val Ala Asp Val Pro Ser Val
210                 215                 220

Ile Ile Ala Arg Thr Asp Ala Glu Ala Ala Thr Leu Ile Thr Ser Asp
225                 230                 235                 240

Val Asp Glu Arg Asp Arg Glu Phe Leu Asp Gly Thr Arg Thr Ala Glu
                245                 250                 255

Gly Phe Phe Gly Val Lys Asn Gly Ile Glu Pro Cys Ile Ala Arg Ala
            260                 265                 270

Lys Ala Tyr Ala Pro Tyr Ala Asp Leu Ile Trp Met Glu Thr Gly Val
        275                 280                 285

Pro Asp Leu Glu Val Ala Lys Lys Phe Ser Glu Ser Val Arg Ser Glu
290                 295                 300

Phe Pro Asp Gln Leu Leu Ala Tyr Asn Trp Ser Pro Ser Phe Asn Trp
305                 310                 315                 320
```

-continued

```
Lys Ala His Leu Asp Asp Ala Thr Ile Ala Lys Phe Gln Lys Glu Leu
                325             330             335

Gly Ala Met Gly Phe Lys Phe Gln Phe Ile Thr Leu Ala Gly Phe His
            340             345             350

Ser Leu Asn Tyr Gly Met Phe Asp Leu Ala Tyr Gly Tyr Ala Gln Asn
        355             360             365

Gln Met Ser Ala Tyr Val Glu Leu Gln Glu Arg Glu Phe Ala Ala Glu
    370             375             380

Glu Arg Gly Tyr Thr Ala Thr Lys His Gln Arg Glu Val Gly Ala Gly
385             390             395             400

Tyr Phe Asp Arg Ile Ala Thr Thr Val Asp Pro Asn Ser Ser Thr Thr
                405             410             415

Ala Leu Thr Gly Ser Thr Glu Glu Gly Gln Phe His
            420             425
```

References

Artman, M., and Bekierkunst, A. (1960) Studies on *Mycobacterium tuberculosis* H37Rv grown in vivo: utilization of glucose. *Proc. Soc. Exp. Biol. Med.* 105: 609–612.

Bange, F.-C., Brown, A. M., and Jacobs, W. R., Jr. (1996) Leucine auxotrophy restricts growth of *Mycobacterium bovis* BCG in macrophages. *Infect. Immun.* 64: 1794–1799.

Clark, D. P. and Cronan, J. E., Jr. (1996) Two-carbon compounds and fatty acids as carbon sources. In *Escherichia coli* and Salmonella: *Cellular and Molecular Biology*. Neidhardt, F. C. (ed.). Washington, D.C.: ASM Press, pp. 343–357.

Clemens, D. L. (1996) Characterization of the *Mycobacterium tuberculosis* phagosome. *Trends Microbiol.* 4: 113–118.

Cronan, J. E., Jr. and LaPorte, D. (1996) Tricarboxylic acid cycle and glyoxylate bypass. In *Escherichia coli* and Salmonella: *Cellular and Molecular Biology*. Neidhardt, F. C. (ed.). Washington, D.C.: ASM Press, pp. 206–216.

Heifets, L. B. and Good, R. C. (1994) Current laboratory methods for the diagnosis of tuberculosis. In *Tuberculosis: Pathogenesis, Protection, and Control*. Bloom, B. R. (ed.). Washington, D.C.: ASM Press, pp. 85–110.

Lee, M. H., Pascopella, L., Jacobs, W. R., Jr., and Hatfull, G. F. (1991) Site-specific integration of mycobacteriophage L5: Integration-proficient vectors for *Mycobacterium smegmatis, Mycobacterium tuberculosis*, and bacille Calmette-Guérin. *Proc. Natl. Acad. Sci. USA* 88: 3111–3115.

McAdam, R. A., Weisbrod, T. R., Martin, J., Scuderi, J. D., Brown, A. M., Cirillo, J. D., Bloom, B. R., and Jacobs, W. R., Jr. (1995) In vivo growth characteristics of leucine and methionine auxotrophic mutants of *Mycobacterium bovis* BCG generated by transposon mutagenesis. *Infect. Immun.* 63: 1004–1012.

Medlar, E. M. (1948) The pathogenesis of minimal pulmonary tuberculosis: a study of 1,225 necropsies in cases of unexpected and sudden death. *Am. Rev. Tuberc.* 58: 583–611.

Mizuguchi, Y., and Tokunaga, T. (1970) Method for isolation of deoxyribonucleic acid from mycobacteria. *J. Bacteriol.* 104: 1020–1021.

Moreira, A. L., Wang, J., Tsenova-Berkova, L., Hellmann, W., Freedman, V. H., and Kaplan, G. (1997) Sequestration of *Mycobacterium tuberculosis* in tight vacuoles in vivo in lung macrophages of mice infected by the respiratory route. *Infect. Immun.* 65: 305–308.

Pelicic, V., Jackson, M., Reyrat, J.-M., Jacobs, W. R., Jr., Gicquel, B., and Guilhot, C. (1997) Efficient allelic exchange and transposon mutagenesis in *Mycobacterium tuberculosis*. *Proc. Natl. Acad. Sci. USA* 94: 10955–10960.

Ratledge, C. (1976) The physiology of the mycobacteria. In *Advances in Microbial Physiology*. Rose, A. H., and Tempest, D. W. (ed.). New York: Academic Press, pp. 115–244.

Segal, W., and Bloch, H. (1956) Biochemical differentiation of *Mycobacterium tuberculosis* grown in vivo and in vitro. *J. Bacteriol.* 72: 132–141.

Segal, W. (1984) Growth dynamics of in vivo and in vitro grown mycobacterial pathogens. In *The Mycobacteria: A Sourcebook*. Kubica, G. P. and Wayne, L. G. (ed.). New York, N.Y.: Marcel Dekker Inc., pp. 547–573.

Snapper, S. B., Melton, R. E., Mustafa, S., Kieser, T., and Jacobs, W. R., Jr. (1990) Isolation and characterization of efficient plasmid transformation mutants of *Mycobacterium smegmatis*. *Mol. Microbiol.* 4: 1911–1919.

Sturgill-Koszycki, S., Schaible, U. E., and Russell, D. G. (1996) Mycobacterium-containing phagosomes are accessible to early endosomes and reflect a transitional state in normal phagosome biogenesis. *EMBO J.* 15: 6960–6968.

Suryanarayana Murthy, P., Sirsi, M., and Ramakrishnan, T. (1973) Effect of age on the enzymes of tricarboxylic acid and related cycles in *Mycobacterium tuberculosis* H37Rv. *Am. Rev. Respir. Dis.* 108: 689–690.

Wayne, L. G., and Lin, K.-Y. (1982) Glyoxylate metabolism and adaptation of *Mycobacterium tuberculosis* to survival under anaerobic conditions. *Infect. Immun.* 37: 1042–1049.

Wayne, L. G. (1994) Cultivation of *Mycobacterium tuberculosis* for research purposes. In *Tuberculosis: Pathogenesis, Protection, and Control*. Bloom, B. R. (ed.). Washington, D.C.: ASM Press, pp. 73–83.

Wheeler, P. R., and Ratledge, C. (1988) Use of carbon sources for lipid biosynthesis in *Mycobacterium leprae*: a comparison with other pathogenic mycobacteria. *J. Gen. Microbiol.* 134: 2111–2121.

Wheeler, P. R. and Ratledge, C. (1994) Metabolism of *Mycobacterium tuberculosis*. In *Tuberculosis:*

*Pathogenesis, Protection, and Control.* Bloom, B. R. (ed.). Washington, D.C.: ASM Press, pp. 353–385.

What is claimed is:

1. A *Mycobacterium tuberculosis* that contains a mutation in its isocitrate lyase gene, wherein the unmutated gene encodes an isocitrate lyase having the amino acid sequence set forth in SEQ ID NO:2 and wherein the mutation is generated using a chemical or recombinant method.

2. The *Mycobacterium tuberculosis* of claim 1, wherein the unmutated gene comprises the nucleotide sequence set forth in SEQ ID NO:1.

3. The *Mycobacterium tuberculosis* of claim 1, wherein the *Mycobacterium tuberculosis* is a recombinant *Mycobacterium tuberculosis*.

4. The *Mycobacterium tuberculosis* of claim 1, wherein the mutation is generated using a chemical method.

5. The *Mycobacterium tuberculosis* of claim 1, wherein the mutation is an allelic exchange, ethyl methane sulfonate, disruption, deletion, insertion, point, substitution, nonsense, missense, polymorphism or rearrangement mutation.

6. The *Mycobacterium tuberculosis* of claim 5, wherein the mutation is a disruption mutation.

7. The *Mycobacterium tuberculosis* of claim 6, wherein the mutation is an allelic exchange mutation.

8. A *Mycobacterium smegmatis* that contains a mutation in its isocitrate lyase gene, wherein the unmutated gene encodes an isocitrate lyase having the amino acid sequence set forth in SEQ ID NO:4 and wherein the mutation is generated using a chemical or recombinant method.

9. The *Mycobacterium smegmatis* of claim 8, wherein the unmutated gene comprises the nucleotide sequence set forth in SEQ ID NO:3.

10. The *Mycobacterium smegmatis* of claim 8, wherein the *Mycobacterium smegmatis* is a recombinant *Mycobacterium smegmatis*.

11. The *Mycobacterium smegmatis* of claim 8, wherein the mutation is generated using a chemical method.

12. The *Mycobacterium smegmatis* of claim 8, wherein the mutation is an allelic exchange, ethyl methane sulfonate, disruption, deletion, insertion, point, substitution, nonsense missense, polymorphism or rearrangement mutation.

13. The *Mycobacterium smegmatis* of claim 12, wherein the mutation is an ethyl methane sulfonate mutation.

* * * * *